United States Patent [19]

Sauli

[11] 4,259,497
[45] Mar. 31, 1981

[54] OXADIAZOLINE-1,3,4 ONE-5S

[75] Inventor: Michel Sauli, Paris, France

[73] Assignee: Philagro, Lyons, France

[21] Appl. No.: 74,307

[22] Filed: Sep. 11, 1979

[30] Foreign Application Priority Data

Sep. 12, 1978 [FR] France ................................ 78 27001

[51] Int. Cl.³ .................... C07D 271/10; A01N 43/82
[52] U.S. Cl. ..................................... 548/144; 424/272
[58] Field of Search ......................................... 548/144

[56] References Cited

U.S. PATENT DOCUMENTS

| 3,846,439 | 11/1974 | Boesch et al. | 548/144 |
| 4,096,273 | 6/1978 | Gutmann | 548/131 |

Primary Examiner—Anton H. Sutto
Attorney, Agent, or Firm—Robert E. Burns; Emmanuel J. Lobato; Bruce L. Adams

[57] ABSTRACT

Novel 1,3,4-oxadiazoline-5-one derivatives, their preparation and the insecticidal compositions in which they are present are disclosed. The novel 1,3,4-oxadiazoline-5-one derivatives correspond to the formula:

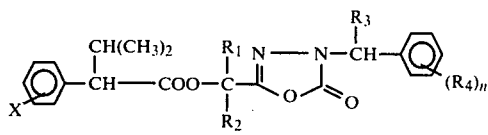

in which:
X represents a halogen atom,
$R_1$, $R_2$ and $R_3$, which may be identical or different, each represent a hydrogen atom or an alkyl radical containing from 1 to 3 carbon atoms,
$R_4$ represents a halogen atom, an alkyl radical containing from 1 to 3 carbon atoms or an alkoxy radical containing from 1 to 3 carbon atoms, and
n represents an integer which is 0, 1, 2, 3 or 4, with the proviso that if n is 2, 3 or 4, the substituents $R_4$ are identical or different. These compounds are useful as agricultural insecticides.

5 Claims, No Drawings

OXADIAZOLINE-1,3,4 ONE-5S

The invention relates to novel 1,3,4-oxadiazolin-5-one derivatives corresponding to the following formula:

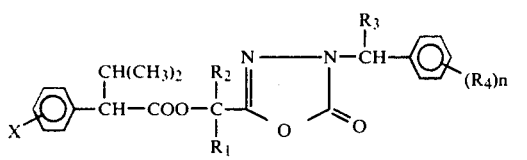

in which
X represents a halogen atom,
R₁, R₂ and R₃, which may be identical or different, each represent a hydrogen atom or an alkyl radical containing from 1 to 3 carbon atoms,
R₄ represents a halogen atom, an alkyl radical containing from 1 to 3 carbon atoms or an alkoxy radical containing from 1 to 3 carbon atoms, and
n is an integer which can be 0, 1, 2, 3 or 4, with the proviso that if n is 2, 3 or 4, the substituents R₄ are identical or different.

The invention also relates to the preparation of the compounds according to formula I. It relates furthermore to the insecticidal compositions which contain, as the active material, at least one compound according to formula I, as well as to the insecticidal treatments carried out with these compositions.

More particularly, the invention relates to the compounds corresponding to the following formula:

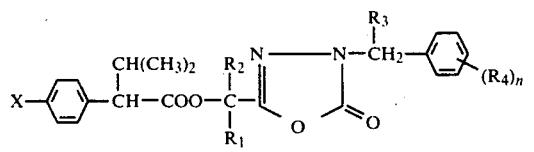

in which X, R₁ and R₂, R₄ and n have the same meaning as in formula I. In formula II, X preferably represents a chlorine atom. The compounds according to formulae I and II all possess at least one asymmetrically substituted carbon atom. Each of these compounds thus exists in several stereoisomeric forms, which also form part of the invention.

Certain oxadiazole derivatives have already been described in the literature because of their insecticidal properties.

Thus, U.S. Pat. No. 4,096,273 describes 3-benzyl-5-[2-(4-chlorophenyl)3-methyl butyryloxy alkyl] 1,2,4-oxadiazole derivatives which can be used as insecticides and correspond to the general formula:

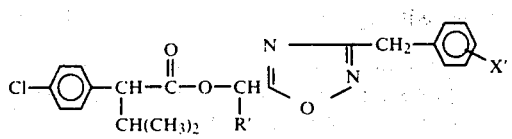

in which R' represents a hydrogen atom or an alkyl radical containing from 1 to 4 carbon atoms and X' represents a hydrogen or chlorine atom.

The compounds according to the invention are different from those described in this United States patent and exhibit a substantially greater insecticidal activity than the said compounds.

The compounds according to formula I can be prepared in accordance with a process which comprises the following stages:

A. Reaction of an alkanoic acid derivative with a benzylhydrazine derivative in accordance with the equation:

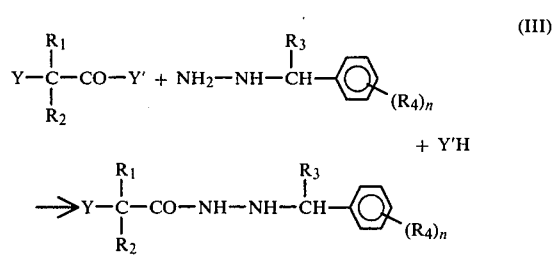

in which:
R₁, R₂, R₃, R₄ and n have the same meaning as in formula I and
Y and Y', which may be identical or different, each represent a chlorine atom or a hydroxyl radical, with the proviso that if Y represents a hydroxyl radical, Y' does not represent a chlorine atom.

B. Cyclization of the compound III resulting from the preceding stage, by reaction with phosgene, in accordance with the equation:

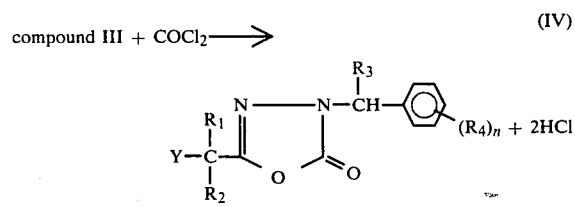

in which R₁, R₂, R₃, R₄ and n have the same meaning as in formula I and Y has the same meaning as above.

C. Reaction of the compound IV resulting from the preceding stage with a derivative of 2-phenyl-3-methyl-butyric acid, of the formula

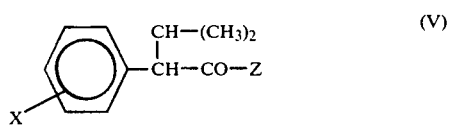

in which X represents a halogen atom and Z, which is different from Y defined above, represents the hydroxyl radical or a chlorine atom, in accordance with the equation:

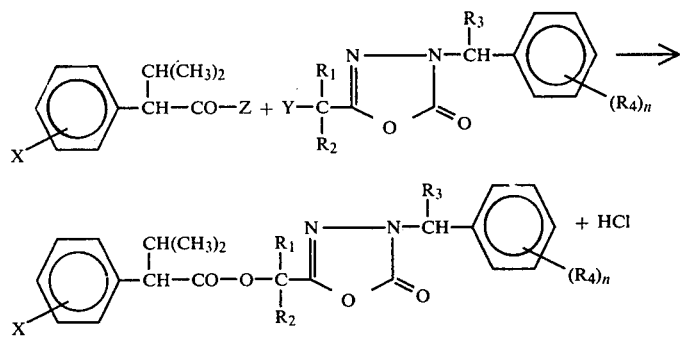

in the presence of a base which serves as an HCl acceptor, such as, e.g., triethylamine, N,N-dimethylaniline or pyridine.

A preferred embodiment of the process described above consists in using, as the starting material for the first stage of the process, an α-chloroalkanoic acid, or a chloride of this acid, of the formula

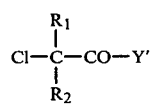  (VI)

in which $R_1$ and $R_2$ have the same meaning as in formula I and Y' represents a hydroxyl radical or a chlorine atom.

According to this preferred embodiment, stage A is carried out in an inert organic solvent medium such as an aromatic or aliphatic hydrocarbon, at a temperature approximately between 10° and 50° C. If compound VI is an acid, the water formed during stage A is removed by azeotropic distillation.

Where this compound VI is an acid chloride, the reaction is preferably carried out in the presence of an arylsulphonic or alkylsulphonic acid, such as methanesulphonic acid.

The cyclization, according to stage B, of the compound thus obtained is carried out in an inert organic solvent medium, e.g. an aromatic hydrocarbon, at a temperature of between 20° and 110° C.

According to stage C of the process, 2-(chloroalkyl)-4-benzyl-1,3,4-oxadiazolin-5-one resulting from stage B is reacted with an acid of the formula:

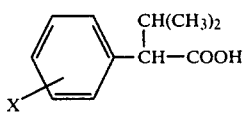  (VII)

in which X has the same meaning as in formula I, in an inert organic solvent medium such as an aromatic or aliphatic hydrocarbon, at a temperature approximately between 10° and 140° C.

According to another embodiment of the process described above, an α-hydroxyalkanoic acid of the formula:

  (VIII)

in which $R_1$ and $R_2$ have the same meaning as in formula I, is used as the starting material for stage A and this stage A is carried out in an organic solvent medium at a temperature approximately between 80° and 150° C., the water formed being removed by azeotropic distillation.

The cyclization, according to stage B of the process, of the compound thus obtained is carried out in an aqueous medium at a temperature of between 10° and 50° C.

According to stage C of the process, the 2-(hydroxyalkyl)-4-benzyl-1,3,4-oxadiazolin-5-one resulting from stage B is reacted with an acid chloride of the formula:

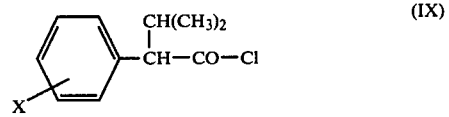  (IX)

in which X has the same meaning as in formula I, in an inert organic solvent medium, such as acetone, methylene chloride or an aromatic hydrocarbon, at a temperature approximately between 10° and 50° C.

The acid according to formula VII is prepared in accordance with the method described in Beilstein 9 I, page 216, for the preparation of 2-phenyl-3-methyl-butyric acid. 2-(4-Chlorophenyl)-3-methyl-butyric acid is a compound which is in itself known and is described in Chem. Abstr. 59, 1016e.

The acid chloride according to formula IX is obtained in accordance with a process which is in itself known, by reaction of thionyl chloride with the acid according to formula VII.

According to a variant of the process described above, which variant also forms part of the invention, the compounds according to formula I, for which $R_3$ represents a hydrogen atom, can also be prepared in accordance with a process which comprises the following stages:

D. Reaction of the hydrazide of an α-hydroxyalkanoic acid with a benzaldehyde derivative to give the hydrazone of this benzaldehyde in accordance with the equation:

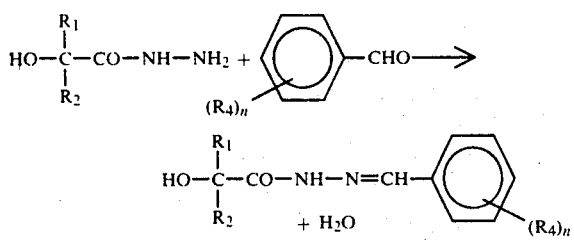

in which $R_1$, $R_2$, $R_4$ and n have the same meaning as in formula I. This reaction takes place in an aqueous-alcoholic medium (e.g. a water/ethanol mixture) in the presence of acetic acid, at a temperature approximately between 20° and 40° C.

E. Reduction, with hydrogen, of the hydrazone resulting from the preceding stage, in accordance with the equation:

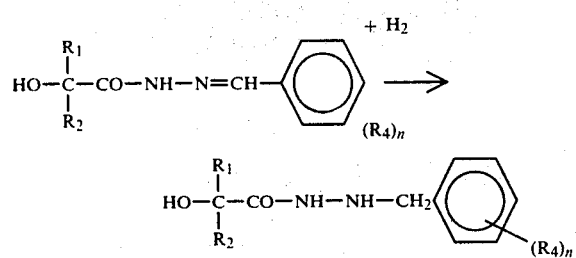

This reduction takes place in the presence of palladium on charcoal, at a temperature approximately between 20° and 60° C.

F. Cyclization of the compound resulting from the preceding stage, by reaction with phosgene, to give a compound of the formula:

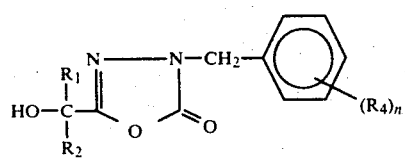

This cyclization takes place in accordance with the same equation, and using the same reaction conditions, as for stage B of the process described above.

G. Reaction of the compound resulting from stage F with a 2-phenyl-3-methyl-butyric acid derivative of the formula:

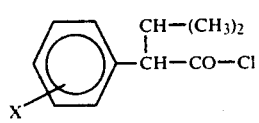

in which X has the same meaning as in formula I.

This reaction takes place in accordance with the same equation, and using the same conditions, as for stage C of the process described above.

The new compounds according to the general formula I exhibit remarkable insecticidal properties. They are particularly active by contact and by ingestion. Particularly valuable results are obtained by means of these compounds in the case of diptera, coleoptera and lepidoptera.

The examples which follow are given to illustrate the invention and do not imply a limitation.

EXAMPLE 1

Preparation of (4-benzyl-1,3,4-oxadiazolin-5-on-2-yl)-methyl 2-(4-chlorophenyl)-3-methyl-butyrate (compound No. 1).

A solution of 2-(4-chlorophenyl)-3-methyl-butyric acid chloride (9.2 g) in acetone (100 cc) is added dropwise, in the course of 10 minutes, to a solution of 2-hydroxymethyl-4-benzyl-1,3,4-oxadiazolin-5-one (8.2 g) and triethylamine (4.04 g) in acetone (100 cc). The mixture is stirred for two hours at room temperature. The precipitate formed is then removed by filtration on a glass frit and the organic solution is concentrated under reduced pressure. The residue is taken up in isopropyl ether (250 cc) and the solution obtained is washed successively with water (200 cc), a 3.6% strength (weight/volume) aqueous hydrochloric acid solution (100 cc), a 4% strength (weight/volume) aqueous sodium hydroxide solution (100 cc) and water (100 cc).

After drying, and concentrating under reduced pressure, the residue obtained is purified by chromatography on a silica column and gives (4-benzyl-1,3,4-oxadiazolin-5-on-2-yl)-methyl 2-(4-chlorophenyl)-3-methyl-butyrate (12 g) melting at 70° C.

| | Elementary composition | |
|---|---|---|
| | calculated | found |
| C% | 62.92 | 62.76 |
| H% | 5.28 | 5.29 |
| 0% | 15.97 | 15.78 |
| N% | 6.99 | 7.03 |
| Cl% | 8.84 | 9.0 |

2-(4-Chlorophenyl)-3-methyl-butyric acid chloride is obtained by reaction of thionyl chloride with 2-(4-chlorophenyl)-3-methyl-butyric acid, melting at 85°, which is itself prepared, in accordance with the method described in Beilstein 9 I - page 216, by reaction of isopropyl bromide with (4-chloro-phenyl)acetonitrile in the presence of sodium amide and hydrolysis of the resulting produce with sulphuric acid.

2-Hydroxymethyl-4-benzyl-1,3,4-oxadiazolin-5-one is prepared as follows:

Benzylhydrazine (61 g) is reacted with glycollic acid (53 g) in solution in toluene (200 cc) at the reflux temperature. After azeotropic distillation of the water formed, the reaction mixture is taken up in water (500 cc). The aqueous layer is decanted and washed with methylene chloride (2×250 cc) and this aqueous layer is then reintroduced into a flask and saturated with phosgene at 20° C. The reaction mixture is taken up in methylene chloride (500 cc) and the organic layer is decanted and washed successively with a solution containing 100 g/l of potassium bicarbonate (500 cc) and then with distilled water (500 cc). After drying over sodium sulphate and concentrating under reduced pressure, 2-hydroxymethyl-4-benzyl-1,3,4-oxadiazolin-5-one (35 g), melting at 54° C., is obtained.

EXAMPLE 2

Preparation of 1-(4-benzyl-1,3,4-oxadiazolin-5-on-2-yl)-ethyl 2-(4-chlorophenyl)-3-methyl-butyrate, in the form of two diastereoisomeric compounds.

A solution of 2-(4-chlorophenyl)-3-methyl-butyric acid chloride (11.6 g) in methylene chloride (100 cc) is added rapidly to a solution of the L-isomer of 2-(1-hydroxyethyl)-4-benzyl-1,3,4-oxadiazolin-5-one (11 g) in methylene chloride (50 cc), and pyridine (4 g) is then added dropwise in the course of 10 minutes. The reaction mixture is stirred for 2 hours at room temperature and is then taken up in a 3.5% strength (weight/volume) aqueous hydrochloric acid solution (300 cc). The organic layer is decanted, washed successively with a 10% strength (weight/volume) aqueous potassium bicarbonate solution (300 cc) and with water (300 cc), and dried.

After filtering, and concentrating under reduced pressure, the residue (weighing 22 g) is purified on a silica column. The oil (17 g) obtained after chromatography gives the following after trituration with petroleum ether:

1-(4-Benzyl-1,3,4-oxadiazolin-5-on-2-yl)-ethyl 2-(4-chlorophenyl)-3-methyl-butyrate (7 g), stereoisomer A (compound No. 2), melting at 102° C., $[\alpha]_D^{20} = -39.6$ (c=10, acetone), and 1-(4-Benzyl-1,3,4-oxadiazolin-5-on-2-yl)-ethyl 2-(4-chlorophenyl)-3-methyl-butyrate (9 g), stereoisomer B (compound No. 3), in the form of a solid paste melting at 40°–45° C., $[\alpha]_D^{20} = -21.3°$ (c=10, acetone).

| | | Elementary composition | |
|---|---|---|---|
| | | found | |
| | calculated | Compound No. | Compound No. 3 |
| C% | 63.69 | 63.69 | 63.26 |
| H% | 5.59 | 5.71 | 5.94 |
| O% | 15.42 | 15.60 | 14.91 |
| N% | 6.75 | 7.01 | 6.17 |
| Cl% | 8.55 | 8.45 | 8.85 |

The L-isomer of 2-(1-hydroxyethyl)-4-benzyl-1,3,4-oxadiazolin-5-one is obtained in accordance with the method described in Example 1 by reacting the L-isomer of lactic acid (33 g) with benzylhydrazine (25 g) in toluene heated to the reflux temperature and then cyclizing the compound obtained with phosgene in an aqueous medium. This gives the L-isomer of 2-(1-hydroxyethyl)-4-benzyl-1,3,4-oxadiazolin-5-one (18 g), melting at 70° C., $[\alpha]_D^{20} = -19°$ (c=10, acetone).

EXAMPLE 3

Following the same procedure as in Example 2, and with the same amounts of reactants, but starting with the D-isomer of 2-(1-hydroxyethyl)-4-benzyl-1,3,4-oxadiazolin-5-one (prepared from the D-isomer of lactic acid), melting at 70° C., $[\alpha]_D^{20} = +19.7°$ (c=10, acetone), Stereoisomer C (compound No. 4) (7 g), melting at 104° C., $[\alpha]_D^{20} = +42°$ (c=10, acetone) and Stereoisomer D (compound No. 5) (9 g), in the form of an oil, $[\alpha]_D^{20} = +22°$ (c=10, acetone), are obtained.

| | | Elementary composition: | |
|---|---|---|---|
| | | found | |
| | calculated | Compound No. 4 | Compound No. 5 |
| C% | 63.69 | 63.89 | 63.90 |
| H% | 5.59 | 5.68 | 6.0 |
| O% | 15.42 | 15.26 | 15.40 |
| N% | 6.75 | 6.93 | 6.16 |
| Cl% | 8.55 | 8.44 | 9.31 |

EXAMPLE 4

Preparation of [4-(2-methylbenzyl)-1,3,4-oxadiazolin-5-on-2-yl]-methyl 2-(4-chlorophenyl)-3-methyl-butyrate (compound No. 6).

A solution of 2-chloromethyl-4-(2-methylbenzyl)-1,3,4-oxadiazolin-5-one (13.3 g) in xylene (35 cc) is added in the course of 20 minutes to a solution of 2-(4-chlorophenyl)-3-methyl-butyric acid (19 g) and triethylamine (11.7 cc) in xylene (175 cc) heated to 110° C. The reaction mixture is heated at the reflux temperature for 4 hours and, after cooling, is washed successively with water (100 cc), a 3.5% strength aqueous hydrochloric acid solution (100 cc), a 4% strength aqueous sodium carbonate solution (100 cc) and water (100 cc). After drying, decolorizing over animal charcoal and concentrating under reduced pressure, the residue obtained is purified by chromatography on a silica column and gives [4-(2-methylbenzyl)-1,3,4-oxadiazolin-5-on-2-yl]-methyl 2-(4-chlorophenyl)-3-methylbutyrate (11.2 g) in the form of an oil.

| | Elementary composition | |
|---|---|---|
| | calculated | found |
| %C | 63.69 | 63.55 |
| %H | 5.59 | 5.78 |
| %O | 15.42 | 15.44 |
| %N | 6.75 | 6.88 |
| %Cl | 8.55 | 9.12 |

2-Chloromethyl-4-(2-methylbenzyl)-1,3,4-oxadiazolin-5-one is prepared as follows: chloroacetyl chloride (56.7 cc) (d=1.42) is reacted with 2-methyl-benzhydrazine (100 g) in solution in toluene (1,000 cc) in the presence of methanesulphonic acid (46.2 cc), at ambient temperature, and phosgene (200 g) is then introduced at a temperature of between 25° and 112° C. The mixture is concentrated and 2-chloromethyl-4-(2-methylbenzyl)-1,3,4-oxadiazolin-5-one (13.3 g) is thus obtained in the form of an oil.

EXAMPLE 5

Preparation of [4-(2-chlorobenzyl)-1,3,4-oxadiazolin-5-on-2-yl]-methyl 2-(4-chlorophenyl)-3-methyl-butyrate (compound No. 7).

Following the procedure of Example 1, starting from a solution of 2-hydroxymethyl-4-(2-chlorobenzyl)-1,3,4-oxadiazolin-5-one (16 g) in acetone (100 cc) and a solution of 2-(4-chlorophenyl)-3-methyl-butyric acid (17.8 g) in acetone (50 cc), [4-(2-chlorobenzyl)-1,3,4-oxadiazolin-5-on-2-yl]-methyl 2-(4-chlorophenyl)-3-methyl-butyrate (26 g) is obtained in the form of an oil.

| Elementary composition | | |
|---|---|---|
| | calculated | found |
| %C | 57.94 | 58.61 |
| %H | 4.63 | 4.68 |
| %O | 14.70 | 13.94 |
| %N | 6.44 | 6.15 |
| %Cl | 16.29 | 16.31 |

2-Hydroxymethyl-4-(2-chlorobenzyl)-1,3,4-oxadiazolin-5-one is obtained by reaction of phosgene with a solution of 1-(2-chlorobenzyl)-2-glycolyl-hydrazine (38 g) in water (600 cc) at a temperature of between 20° and 30°.

In this way, after recrystallization from isopropyl ether, 2-hydroxymethyl-4-(2-chlorobenzyl)-1,3,4-oxadiazolin-5-one (16 g), melting at 67° C., is obtained (yield = 42%).

1-(2-Chlorobenzyl)-2-glycolyl-hydrazine is prepared by reducing 2-chlorobenzaldehyde glycolylhydrazone (41.5 g), dissolved in dioxane (415 cc), with hydrogen in the presence of palladium on charcoal in an autoclave, under hydrogen at a pressure of 15 kg/cm², at a temperature of between 20° and 60° C. After filtration and concentration, 2-hydroxymethyl-4-(2-chlorobenzyl)-1,3,4-oxadiazolin-5-one (38 g) is obtained.

2-Chlorobenzaldehyde glycolylhydrazone (41.5 g), melting at 166° C., is itself obtained by reaction of glycolylhydrazine (18 g) with 2-chlorobenzaldehyde (30.9 g) dissolved in a mixture of water (20 cc), acetic acid (10 cc) and ethanol (60 cc), at a temperature of between 20° and 40° C.

After precipitation and cooling, the product is filtered off, washed with water and alcohol, and dried. [4-(2-Chlorobenzyl)-1,3,4-oxadiazolin-5-on-2-yl]-methyl 2-(4-chlorophenyl)-3-methyl-butyrate (41.5 g) is thus obtained.

EXAMPLE 6

The following compounds were prepared from suitable starting materials by employing the method described in Example 4:

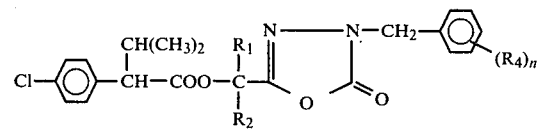

| Compound No. | R₁ | R₂ | (R₄)ₙ | Melting point | Elementary composition | | |
|---|---|---|---|---|---|---|---|
| | | | | | | calculated | found |
| 8 | H | H | —⌬—Cl | oil | C % | 57.94 | 58.54 |
| | | | | | H % | 4.63 | 4.85 |
| | | | | | O % | 14.70 | 14.80 |
| | | | | | Cl % | 16.29 | 15.80 |
| | | | | | N % | 6.44 | 6.29 |
| 9 | CH₃ | CH₃ | —⌬ | 85° C. | C % | 64.41 | 63.86 |
| | | | | | H % | 5.87 | 5.87 |
| | | | | | O % | 14.92 | 14.91 |
| | | | | | Cl % | 8.27 | 8.98 |
| | | | | | N % | 6.53 | 6.04 |
| 10 | H | H | —⌬-OCH₃ | oil | C % | 61.32 | 62.90 |
| | | | | | H % | 5.38 | 5.65 |
| | | | | | O % | 18.57 | 18.17 |
| | | | | | Cl % | 8.23 | 7.70 |
| | | | | | N % | 6.50 | 5.90 |
| 11 | H | H | —⌬—CH₃ | oil | C % | 63.69 | 63.22 |
| | | | | | H % | 5.99 | 5.48 |
| | | | | | O % | 15.42 | 14.81 |
| | | | | | Cl % | 8.55 | 9.25 |
| | | | | | N % | 6.75 | 7.18 |
| 12 | H | H | —⌬-CH₃ | oil | C % | 63.69 | 62.50 |
| | | | | | H % | 5.59 | 5.40 |
| | | | | | O % | 15.42 | 15.02 |
| | | | | | Cl % | 8.55 | 10.02 |
| | | | | | N % | 6.75 | 7.70 |
| 13 | H | H | —⌬-OCH₃ | oil | C % | 61.32 | 61.76 |
| | | | | | H % | 5.38 | 5.37 |
| | | | | | O % | 18.57 | 18.0 |
| | | | | | Cl % | 8.23 | 6.50 |
| | | | | | N % | 6.50 | 6.0 |
| 14 | H | H | —⌬-Cl | oil | C % | 57.94 | 58.20 |
| | | | | | H % | 4.63 | 4.64 |
| | | | | | O % | 14.70 | 14.12 |
| | | | | | Cl % | 16.29 | 16.70 |
| | | | | | N % | 6.44 | 6.28 |

EXAMPLE 7

Contact-insecticidal activity (flies and flour beetles).

An acetone solution or suspension (1 cc) containing a given concentration of the product to be studied is introduced into a 120 cc glass pot and four pots are prepared in this way for each concentration of the product to be studied. When the solvent has evaporated off, either 5 flies (Musca domestica) or 10 flour beetles (Tribolium confusum) are introduced into each of the pots. For each concentration of the product to be studied, two pots are used per species of insect. The pots are covered with a wire mesh and the number of dead insects after 24 hours' contact, in the case of the flies, and after 3 days' contact, in the case of the flour beetles, is counted. The concentration which causes the death of 90% of the insects, hereafter referred to as $Cl_{90}$, is thus determined. The results observed are shown in the table below, in which the $Cl_{90}$ values are expressed in mg per cc, taking compound No. 1 of U.S. Pat. No. 4,096,273 as the comparison product.

| Compound No. | Flies $Cl_{90}$ | Flour beetles $Cl_{90}$ |
|---|---|---|
| 1 | 10 | 100 |
| 3 | 30 | 300 |
| 5 | 100 | — |
| 6 | 100 | — |
| 11 | 200 | — |
| 12 | 100 | — |
| 13 | 1,000 | — |
| Comparison compound | 30 | 1,000 |

EXAMPLE 8

Insecticidal activity by contact-ingestion (leaves treated by dipping and exposed to caterpillars of *Plutella maculipennis* and caterpillars of *Pieris brassicae*).

An emulsifiable solution having the following composition is prepared:
active material to be tested—250 g
emulsifier (a mixture of calcium phenylsulphonate and of oxyethyleneated nonylphenol)—90 g
surface-active agent (monolaurate of oxyethyleneated sorbitan)—20 g
solvent (mixture of 2 volumes of acetophenone and 3 volumes of toluene)—q.s.p.—1,000 cc The solution thus obtained is then diluted with distilled water containing 0.02% of the same surface-active agent, so as to give several solutions of a defined concentration.

Young leaves of broccoli (*Brassica oleracea*) at the four-leaf stage are dipped for 10 seconds in the solutions to be studied. The leaves are allowed to dry and when they are dry they are spread in cylindrical plastic boxes. Ten caterpillars (3rd stage) of *Plutella maculipennis* or of *Pieris brassicae* are placed in each box. For each species of caterpillar, two boxes are used per concentration of active material.

After 3 days, the living caterpillars and the dead caterpillars are counted for each concentration of active material, and the concentration which results in the death of 50% of the caterpillars ($Cl_{50}$) is determined. The results observed are shown in the table below, in which the $Cl_{50}$ are expressed in mg per cc:

| Compound No. | Plutella ($Cl_{50}$) | Pieris ($Cl_{50}$) |
|---|---|---|
| 1 | 20 | 100 |
| 2 | 1,000 | 1,000 |
| 3 | 100 | 300 |
| 5 | 1,000 | — |
| 8 | 1,000 | — |
| 10 | 2,000 | 2,000 |
| 11 | 2,000 | — |
| 12 | 1,000 | 2,000 |
| 13 | 300 | 1,000 |
| Comparison product | 300 | 500 |

For use in practice, the compounds according to the invention are rarely used by themselves. Most commonly, they form a component of compositions which in general comprise a carrier and/or a surface-active agent in addition to the active material according to the invention. In these compositions, the content of active material can vary from 0.05% by weight to 95% by weight.

The term "carrier" in the sense of the present description denotes an organic or inorganic, natural or synthetic, material with which the active material is associated in order to facilitate its application to the plant, to seeds or to the soil, or to facilitate its transportation or its handling. The carrier can be solid (clays, natural or synthetic silicates, calcined magnesia, kieselguhr, tricalcium phosphate, cork powder, absorbent charcoal, resins, waxes, solid fertilisers or the like) or fluid (water, alcohols, ketones, petroleum fractions, chlorinated hydrocarbons and liquefied gases).

The surface-active agent can be an emulsifier, dispersing agent or wetting agent and can be ionic or non-ionic. Examples which may be mentioned are salts of polyacrylic acids or ligninsulphonic acids, sulphoricinoleates, quaternary ammonium salts, ethylene oxide condensates with fatty alcohols, fatty acids or fatty amines and, in particular products based on ethylene oxide condensates, such as condensates of ethylene oxide with octylphenol, or esters of fatty acids and anhydro-sorbitols which have been rendered soluble by etherification of the free hydroxyl radicals by condensation with ethylene oxide. It is preferable to use agents of the non-ionic type because they are not sensitive to electrolytes.

The compositions according to the invention can be prepared in the form of wettable powders, dusting powders, granules, solutions, emulsifiable concentrates, emulsions, suspension concentrates and aerosols.

The wettable powders according to the invention can be prepared in such a way that they contain from 20 to 95% by weight of active material, and they usually contain from 3 to 10% by weight of a dispersing agent and, where necessary, from 0 to 10% by weight of one or more stabilizers and/or other additives, such as penetrating agents, adhesives, anti-caking agents, dyestuffs and the like.

By way of example, the following is the composition of a wettable powder, the percentages being expressed by weight:
active material (compound No. 6)—50 g
calcium lignosulphonate (deflocculating agent)—5%
isopropylnaphthalenesulphonate (wetting agent)—1%
anti-caking silica—5%
filler (kaolin)—39%

The dusting powders are usually prepared in the form of a dust concentrate which has a composition similar to that of a wettable powder, but without a dispersing agent. They can be diluted on site by means of a supplementary amount of a fluid carrier, so that a composition is obtained which can easily coat the seeds to be treated and which usually contains from 0.5 to 10% by weight of active material.

By way of example, the following is the composition of a dusting powder:
active material (compound No. 6)—50%
anionic wetting agent—1%
anti-caking silica—6%
kaolin (filler)—43%

The granules, intended to be scattered on the ground, are usually prepared so that they have a size of between 0.1 and 2 mm, and can be manufactured by agglomeration or by impregnation. In general, the granules contain from 0.5 to 25% of active material, and from 2 to 20% by weight/volume of suitable additives, such as stabilizers, modifiers which ensure slow liberation, binders and solvents.

The emulsifiable concentrates which can be applied by spraying usually contain a solvent, a co-solvent where necessary, from 10 to 50% by weight/volume of active material and from 2 to 20% by weight/volume of suitable additives, such as stabilizers, penetrating agents, corrosion inhibitors, dyestuffs and adhesives.

By way of example, the following is the composition of an emulsifiable concentrate, the amounts being expressed in g/liter:
active material (compound No. 6)—400 g/l
dodecylbenzenesulphonate—24 g/l
nonylphenol oxyethyleneated with 10 molecules of ethylene oxide—16 g/l
cyclohexanone—200 g/l
aromatic solvent q.s.p.—1 liter Aqueous dispersions and emulsions, e.g. compositions obtained by diluting a wettable powder or an emulsifiable concentrate according to the invention with water, are included in the general scope of the present invention. These emulsions can be of the water-in-oil type or of the oil-in-water type and can have a thick consistency such as that of a "mayonnaise".

For so-called "ultra-low volume" application, with a spray of very fine droplets, solutions in organic solvents containing from 70 to 99% of active material are prepared.

The compositions according to the invention can contain other ingredients, e.g. protective colloids, adhesives or thickeners, as well as other known active materials possessing pesticidal properties, in particular insecticidal or fungicidal properties.

I claim:

1. 1,3,4-Oxadiazolin-5-one derivative of the formula:

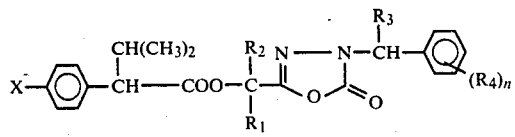

in which
X represents a halogen atom,
$R_1$, $R_2$ and $R_3$, which may be identical or different, each represent a hydrogen atom or an alkyl radical containing from 1 to 3 carbon atoms;
$R_4$ represents a halogen atom, an alkyl radical containing from 1 to 3 carbon atoms or an alkoxy radical containing from 1 to 3 carbon atoms, and
n represents an integer which is 0, 1, 2, 3 or 4, with the proviso that if n is 2, 3 or 4, the substituents $R_4$ are identical or different.

2. A compound according to claim 1, in which X represents a chlorine atom.

3. A compound according to claim 1, wherein X represents a chlorine atom and $R_4$ represents a chlorine atom, an alkyl radical containing 1 to 3 carbon atoms or an alkoxy radical containing from 1 to 3 carbon atoms.

4. A compound according to claim 1, wherein X represents a chlorine atom, $R_4$ represents a chlorine atom, a methyl group or a methoxy group and n is 0 or 1.

5. A compound according to claim 1, which is (4-benzyl-1,3,4-oxadiazolin-5-on-2-yl)-methyl 2-(4-chlorophenyl)-3-methyl-butyrate.

* * * * *